(12) United States Patent
Hille et al.

(10) Patent No.: US 6,868,286 B1
(45) Date of Patent: Mar. 15, 2005

(54) DEVICE FOR A TRANSDERMAL AND PHONOPHORETIC COMBINATION THERAPY AND THE USE THEREOF IN A METHOD FOR MEDICAL APPLICATION

(75) Inventors: Thomas Hille, Neuwied (DE); Bernhard Hehn, Ingelheim (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/830,780

(22) PCT Filed: Oct. 23, 1999

(86) PCT No.: PCT/EP99/08042

§ 371 (c)(1),
(2), (4) Date: May 1, 2001

(87) PCT Pub. No.: WO00/25762

PCT Pub. Date: May 11, 2000

(30) Foreign Application Priority Data

Nov. 3, 1998 (DE) .......................................... 198 50 517

(51) Int. Cl.⁷ ................................................. A61N 1/30
(52) U.S. Cl. .......................... 604/20; 604/19; 604/500; 604/501
(58) Field of Search ............................. 604/19, 20, 21, 604/500, 501, 511, 502, 93.01, 890.1, 891.1, 22, 65, 66, 67; 607/120, 901, 154; 601/2, 17

(56) References Cited

U.S. PATENT DOCUMENTS

| 4,767,402 A | * | 8/1988 | Kost et al. ..................... 604/22 |
| 4,948,587 A | * | 8/1990 | Kost et al. ..................... 424/435 |
| 5,115,805 A | | 5/1992 | Bommannan et al. |
| 5,415,629 A | * | 5/1995 | Henley .......................... 604/20 |
| 5,756,117 A | * | 5/1998 | D'Angelo et al. ........... 424/449 |
| 6,041,253 A | * | 3/2000 | Kost et al. ..................... 604/20 |
| 6,234,990 B1 | * | 5/2001 | Rowe et al. ................... 604/22 |
| 6,689,380 B1 | * | 2/2004 | Marchitto et al. ........... 424/449 |

FOREIGN PATENT DOCUMENTS

| CA | 2030178 | 8/1995 |
| DE | 39 39 376 C1 | 5/1991 |
| DE | 691 24 365 T2 | 5/1997 |
| EP | 0 278 074 A2 | 8/1988 |
| WO | WO 90/01971 | 3/1990 |
| WO | WO 97/04832 | 2/1997 |
| WO | WO 99/39763 | 8/1999 |

OTHER PUBLICATIONS

Miyazaki, et al., External Control of Drug Release and Penetration. VI. Enhancing Effect of Ultrasound on the Transdermal Absorption of Indomethacin from an Ointment in Rats, Chemical and Pharmaceutical Bulletin, JP, Pharmaceutical Society of Japan, Oct. 1, 1992.

* cited by examiner

*Primary Examiner*—Manuel Mendez
(74) *Attorney, Agent, or Firm*—Frommer Lawrence & Haug LLP

(57) ABSTRACT

The invention relates to a combination therapy by TTS and simultaneous initial ultrasound treatment and the subsequent use of the TTS without additional ultrasound treatment. The treatment is characterized in that it shows an effect without or with only little delay. This form of therapy is especially advantageous for treating strong or chronic pains. The invention relates to a corresponding device and the use of suitable pharmaceutical substances.

21 Claims, No Drawings

DEVICE FOR A TRANSDERMAL AND PHONOPHORETIC COMBINATION THERAPY AND THE USE THEREOF IN A METHOD FOR MEDICAL APPLICATION

The invention relates to the transdermal administration of pharmaceuticals. In particular, the invention relates to a combination treatment by means of TTS and simultaneous, initial treatment by means of ultrasound and the subsequent application of the TTS without additional ultrasonic treatment, the action of the TTS commencing without or only with a slight time delay. The therapy form is particularly advantageous for the treatment of severe or chronic pain.

The doubtless great advantages which the transdermal administration of pharmaceuticals (pharmaceutical active compounds) has is often confronted as a disadvantage with not only the qualitative and quantitative limitation of the amount of pharmaceutical which can be absorbed through the skin, but also that the absorption through the skin only commences with a great time delay. It is known to the person skilled in the art that the skin is not an absorption organ, but rather has the object of preventing the penetration of foreign bodies, i.e. also of pharmaceuticals.

As these facts are known to the person skilled in the art, the concept of the so-called lag-time was coined. This is understood as meaning the time which lies between the first administration of a transdermally administrable medicament (e.g. of a TTS) and the first occurrence of a measurable plasma concentration or the first occurrence of the expected physiological action of the pharmacon. This lag-time is particularly critical if a pharmaceutical is to be administered not only chronically for continuous use, i.e. is intended to be administered over a relatively long period of time, but if at the same time it is also required that its action occurs as immediately as possible after the first administration of the medicament, e.g. in the administration of centrally active analgesics.

The disadvantageous lag-time can actually be avoided or reduced, when administering a TTS for the first time, by additionally administering a medicament having a rapid release of active compound, e.g. an oral pharmaceutical form or an intravenous injection. Such a combined administration of different medicaments, however, is not unproblematical, as the point of a TTS lies in the system-controlled delivery of pharmaceuticals. This means that the active compound should simply not be rapidly released.

Therefore, at the same time as the start of the development of therapies by means of dermal or transdermal application, ways were sought of increasing the penetrability or penetration rate of pharmaceuticals through the skin. An approach to a solution was first seen in the development of penetration promoters (enhancers), which are added to the medicaments for dermal or transdermal administration. These substances alter, for at least a short period of time, relatively deep-seated skin structures and can lead to undesired side effects in unfavorable cases.

Other possibilities for increasing the absorption rate of pharmaceuticals consist in the removal of the stratum corneum by laser treatment or by repeated sticking-on and tearing-off of adhesive strips, so-called stripping. Although these two treatment methods do also shorten the lag-time, it is disadvantageous in this process that not only the desired penetration of the pharmaceutical, but that also an undesired penetration of other constituents of the medicament, as well as of microorganisms such as bacteria and fungal spores, into the human body is facilitated.

A further way of improving the dermal absorption rate consists in the use of current. This process, known under the term iontophoresis, cannot be used without pain, as is known to the medical expert.

It is likewise not possible to use the so-called prickle patch without pain. This form of a dermal medicament is attached to the body using needles which penetrate the horny layer of the skin. The release of active compound takes place through the needles, which serve as an attachment aid at the same time. It is obvious that the discussion here can no longer be of dermal administration in the conventional sense of the word, but of subcutaneous injection of a pharmaceutical, with all its known disadvantages (necessity of sterile needles, no protracted release etc.).

An alternative which is of interest at first glance is so-called phonophoresis or sonophoresis. These are understood as meaning the introduction of pharmaceuticals through the living skin into underlying tissue by means of ultrasound. Beyond a number of different studies in orthopedics and sports medicine, a routine therapeutic use is not known.

In most in-vivo studies, the active principles employed were vitamins such as thiamine and ascorbic acid, antiinflammatories, insulin, antibiotics, chemotherapeutics and local anesthetics. The administration forms used here were solutions or semi-solid formulations such as ointments and gels, which were combined with stationary ultrasonic sources.

The present invention relates to the use of dermal or transdermal therapeutic systems (TTS, e.g. of the reservoir or matrix type) in combination with an ultrasonic source. Up to now, it is not known that in-vivo studies of this type have been carried out.

The object of the invention is therefore the provision of a medicament and of a process for the transdermal administration of pharmaceuticals, the lag-time outlined above being so far reduced that the physiological action of the pharmaceutical after transdermal administration commences immediately or with an acceptable, i.e. significantly reduced, lag-time.

Furthermore, the object consists in making available a device and a process in order to make possible, to patients with chronic pain, a long-term treatment with centrally active analgesics, which begins without or with a very short lag-time. At the same time, the disadvantages of the sonophoretic devices and processes known in the prior art are to be avoided.

The object is achieved according to the invention by a device for transdermal therapy, which comprises a transdermal therapeutic system (TTS) having a pharmaceutical active compound and an ultrasonic source contained therein. One particular embodiment of this device contains an active compound which has such a low skin penetration rate (permeation rate) that the sole administration of such a TTS does not lead to the achievement of a physiological action without or within an acceptable, i.e. sufficiently short, lag-time. In a preferred embodiment, the device additionally contains a means for improving the ultrasonic transfer, e.g. a contact gel.

By means of the invention, a process for the administration of a transdermally administrable active compound, in particular of one with a low skin penetration rate, is furthermore made available, which comprises the steps:

1.) sticking of a patch containing the transdermally administrable active compound onto the skin,
2.) the treatment of this skin-adherent patch with ultrasound during an initial phase, and 3.) the wearing of the patch during a subsequent long-term phase without additional ultrasonic treatment.

In a preferred embodiment, a means of improving the transfer of ultrasound, e.g. a contact gel, is applied to this patch after the sticking of the patch containing the active compound onto the skin. Said initial phase begins immediately after application of the patch to the skin of the patient.

The invention furthermore describes a novel use of a transdermally administrable active compound for the production of a medicament which is used in a transdermal therapy in which, in an initial phase, an ultrasonic treatment of the administered pharmaceutical takes place and, during a subsequent long-term phase, the active compound is delivered onto and through the skin of the patient from this medicament without additional ultrasonic treatment.

Finally, the invention makes available a new use of ultrasound, which is employed in a transdermal therapy. Here, the ultrasound is transmitted to the applied TTS in an initial phase, while in a subsequent long-term phase further treatment with ultrasound is discontinued. Here too, in a particular embodiment the additional use of a contact gel can make possible an improved exposure to the ultrasound on the skin area under the TTS.

The present invention is all the more surprising, as in the patent literature numerous sonophoretic systems are indeed described in which the disadvantages of ultrasonic treatment, e.g. the lacking transportability, are mentioned, but are not taken into account. It is therefore by no means surprising that up to now, on account of these disadvantages, a sonophoretic system has neither found its way into the forms of medicinal therapy used in practice, nor that the licensing of a sonophoretic system has been applied for or granted.

The combination treatment by means of TTS and an initial treatment by ultrasound, if appropriate with contact gel, and the subsequent use of the TTS without additional ultrasonic treatment is thus a completely new concept for the long-term treatment of a patient, the action commencing without or only with a slight time delay. Fundamentally, this form of therapy can be employed in any long-term treatment which requires a continuous absorption of active compound. The form of therapy is particularly advantageous in the treatment of severe or chronic pain. The objective set is thus achieved in an optimal manner.

In the following text, the specialist terms used will be explained in greater detail.

The term medicaments is known to the person skilled in the art. These are understood as meaning substances or substance mixtures for human or veterinary medicine. They consist of the pharmaceutical active compound(s) (pharmaceutical, pharmacon) and other customary constituents which make this active compound pharmaceutically utilizable.

The pharmaceutical active compounds which can be used according to the invention are those which are transdermally administrable. In particular, the transdermally administrable active compounds are also included which have a comparatively low skin penetration rate and consequently cause a high lag-time on transdermal use thereof.

Ointments, which are gels of plastic deformability, are suitable for application to the skin or to mucous membranes (e.g. nose, eye, mouth, stomach), as well as pastes, which can be described as ointments having a high proportion of solid.

According to Zaffaroni, a transdermal therapeutic system (TTS) should be understood as meaning "a pharmaceutical-containing device or an administration form which delivers one or more pharmaceuticals at a predetermined rate continuously over a fixed period of time at a defined administration site" (cited by Heilmann, therapeutische Systeme—Konzept und Realisation programmierter Arzneiverabreichung [Therapeutic Systems—Concept and Realization of Programmed Pharmaceutical Administration] 4$^{th}$ edition, Ferdinand Enke-Verlag Stuttgart 1984, page 26), the application site in the present case being the skin. The construction of transdermal systems is known to the person skilled in the art, e.g. from Y. W. Chien: "Developmental Concepts and Practice in Transdermal Therapeutic Systems", in: Transdermal Controlled Systemic Medications, ed. by Y. W. Chien, Marcel Dekker, Inc., New York 1987.

Patents in which the fundamental construction is described are, for example, DE 33 15 272, DE 38 43 239, EP 261 402, U.S. Pat. No. 3,598,122. If a transdermal therapeutic system is applied to the skin of a patient, the active compound should be delivered in order to be topically (i.e. locally or regionally) or systemically active in the patient. Pharmaceutical forms of this type are already utilized therapeutically. They are mostly constructed in layer form and in the simplest case consist of a backing layer, a self-adhesive active compound reservoir, if appropriate with an additional membrane controlling the release rate, and a protective layer, again detachable, which is to be removed before application. The active compounds used are substances which, applied to the skin without or with a control membrane, cause a local or systemic action. Substances having local action are, for example, antiperspirants, fungicides, bactericides and bacteristatics. Substances having systemic action are, for example, antibiotics, hormones, antipyretics, antidiabetics, coronary dilators, cardioactive glycosides, spasmolytics, antihypertensives, psychopharmaceuticals, migraine agents, corticoids, contraceptives, antirheumatics, anticholinergics, sympatholytics, sympathomimetics, vasodilators, anticoagulants and analgesics.

Analgesics, in the sense of the present invention, means pharmaceuticals which reduce or suppress sensitivity to pain in therapeutic doses. These include, in particular, centrally acting, potent analgesics (hypnoanalgesics, opiates). This group of pharmaceutical active compounds includes, inter alia, morphine, heroin and other derivatives of morphine; dihydromorphine derivatives such as hydromorphone, oxycodone; morphinan derivatives such as levorphanol, buprenorphine; analgesics of the pethidine groups such as pethidine, ketobemidone; methadone and derivatives such as levomethadone, dextromoramide; fentanyl and its derivatives; benzomorphan derivatives such as pentazocine; and phenylaminocyclohexenyl derivatives such as tilidine.

It is obvious that the practical use of the present invention is of particular importance for the administration of analgesics, since in the acute state of pain it is unreasonable for the patient to wait to the end of the lag-time until the action of the medicament commences. In such a case, a possible acceptable lag-time is a period of up to a few minutes.

An agent improving the transmission of ultrasound is intended to mean a substance or a substance mixture which makes possible or facilitates the diffusion of ultrasonic waves or decreases or prevents a weakening in intensity. Such substances or substance mixtures include, for example, contact gels such as, for example, contact gel according to GP 10.

The device for transdermal therapy according to the invention comprises a transdermal therapeutic system (TTS)

containing an active compound having a low skin penetration rate and a sound source for ultrasound. In a particular embodiment, the device further contains an agent for improving ultrasound transmission. Such an agent improving the transmission of ultrasound is, for example, an aqueous contact gel. In further embodiments, the TTS contains a layer of a pressure-sensitive adhesive, a porous layer or a layer of a hydrogel. The device can contain an analgesic as a pharmaceutical active compound having a low skin penetration rate. The active compound contained in the device according to the invention can be selected from the group consisting of morphine, heroin, the derivatives of morphine, the dihydromorphine derivatives, hydromorphone, oxycodone, the morphinan derivatives, levorphanol, buprenorphine, the pethidine group, pethidine, ketobemidone, methadone, levomethadone, dextromoramide, fentanyl and its derivatives, the benzomorphan derivatives, pentazocine, the phenylaminocyclohexenyl derivatives and tilidine.

The device according to the invention can contain an ultrasound source which generates ultrasound in a frequency range from 20 kHz to 10 MHz. In a preferred embodiment, ultrasound is generated in a frequency range from 40 kHz to 1 MHz. In a particularly preferred device, ultrasound is generated in a frequency range from 800 kHz to 1 MHz. The intensity of the ultrasound used is between 0.1 and 3 W/cm$^2$.

The invention also relates to the use of a transdermally administrable active compound having a low skin penetration rate for the production of a medicament for use in transdermal therapy and which comprises an initial phase, in which, as a consequence of ultrasonic treatment, the transdermally administrable active compound has an increased skin penetration rate, and a subsequent long-term phase, in which the transdermally administrable active compound is delivered onto and through the skin without additional ultrasonic treatment. In a particular embodiment, the medicament is a transdermal therapeutic system (TTS). Such a TTS can have a pressure-sensitive contact adhesive layer, a porous layer or a hydrogel layer.

In a particular embodiment, the transdermal therapy can be one wherein the initial phase is extended over a period of 1 to approximately 180 minutes. In a preferred embodiment, the initial phase extends over a period of 1 to approximately 60 minutes. In a particularly preferred embodiment, the initial phase extends over a period of 1 to approximately 30 minutes. In a very particularly preferred embodiment, the initial phase extends over a period of 1 to approximately 10 minutes.

In an embodiment of the invention, the ultrasonic treatment is carried out using a frequency from the range between 20 kHz and 10 MHz. In a preferred embodiment, the ultrasonic treatment is carried out using a frequency from the range between 40 kHz and 1 MHz, particularly preferably using a frequency from the range between 800 kHz and 1 MHz.

According to the invention, the ultrasonic treatment is carried out using an intensity of between 0.01 and 3.0 W/cm$^2$. In a preferred form of the invention, the transdermal therapy is used for the treatment of pain, the transdermally administrable active compound with a low skin penetration rate being an analgesic. In a preferred embodiment of the invention, an active compound from the group consisting of morphine, heroin, the derivatives of morphine, the dihydromorphine derivatives, hydromorphone, oxycodone, the morphinan derivatives, levorphanol, buprenorphine, the pethidine group, pethidine, ketobemidone, methadone, levomethadone, dextromoramide, fentanyl and its derivatives, the benzomorphan derivatives, pentazocine, the phenylaminocyclohexenyl derivatives and tilidine is used. In a further embodiment, an agent improving the transmission of ultrasound is additionally employed, which can be, for example, an aqueous contact gel.

The invention relates to a process for the administration of a transdermally administrable active compound having a low skin penetration rate, which comprises the steps:
 a) sticking of a patch containing the transdermally administrable active compound onto the skin,
 b) treatment of the skin-adherent patch with ultrasound during an initial phase, and
 c) wearing of the patch during a subsequent long-term phase without additional ultrasonic treatment.

In an embodiment, the patch used in the process is a transdermal therapeutic system (TTS). Suitable patches can contain a layer having a pressure-sensitive contact adhesive, a porous layer or a layer containing a hydrogel. The process according to the invention has an initial phase which extends over a period of 1 to approximately 180 minutes, preferably over a period of 1 to approximately 60 minutes, particularly preferably over a period of 1 to approximately 30 minutes and very particularly preferably over a period of 1 to approximately 10 minutes. The subsequent long-term treatment can extend over a period of one or more, for example 3 or 7 days.

In an embodiment of the process, the ultrasonic treatment is carried out using a frequency from the range between 20 kHz and 10 MHz. In a preferred embodiment, the ultrasonic treatment is carried out using a frequency from the range between 40 kHz and 1 MHz and in a particularly preferred embodiment using a frequency from the range between 800 kHz and 1 MHz. According to the invention, the ultrasonic treatment in the process is carried out using an intensity between 0.01 and 3 W/cm$^2$.

In the process, an agent improving the transmission of ultrasonic waves can additionally be applied to the patch adhering to the skin of the patient. Such an agent improving the transmission of ultrasound can be an aqueous contact gel.

In a particular embodiment of the process according to the invention, this is used for the treatment of pain. These pains can be chronic and/or acute states of pain.

In an embodiment of the process, the transdermally administrable active compound with a low skin penetration rate is an analgesic. In a further embodiment of this process, the active compound is selected from the group consisting of morphine, heroin, the derivatives of morphine, the dihydromorphine derivatives, hydromorphone, oxycodone, the morphinan. derivatives, levorphanol, buprenorphine, the pethidine group, pethidine, ketobemidone, methadone, levomethadone, dextromoramide, fentanyl and its derivatives, the benzomorphan derivatives, pentazocine, the phenylaminocyclohexenyl derivatives and tilidine.

Furthermore, the invention relates to the use of ultrasound for increasing the skin penetration rate of a transdermally administrable active compound in a process for transdermal therapy, wherein, in an initial phase, ultrasound acts on the active compound situated in contact with the skin, and in a subsequent long-term phase, the ultrasonic treatment of the active compound is discontinued.

The invention is illustrated by the following example:

One buprenorphine-containing TTS each, as described in DE 39 39 376, is stuck onto a piece of human skin. Skin and TTS are placed on a so-called Franz's diffusion cell. One TTS, called sample A below, is coated with contact gel, Carbopol GP 10. This sample A is treated with ultrasound for 15 minutes (apparatus: Nemectroson, model 2, from Nemectroson GmbH, Karlsruhe, intensity 1.5 watts/cm$^2$, operating mode 10%, 100 kHertz). The sample B is not treated with ultrasound.

After 1 or 2 or 3 hours, the concentration of buprenorphine base in the acceptor medium of the Franz's diffusion cell is determined and the absorption rate is established from this. The values found are shown in Table 1.

It is clearly seen that in the case of the 15-minute treatment with ultrasound, the absorption rate within the first hour is increased by a factor of 40. Table 1: Penetration of buprenorphine from a TTS through human skin with (sample A) and without (sample B) initial ultrasonic treatment.

| Sample name | Accumulated buprenorphine permeation [in µg/mm$^2$] | | |
| --- | --- | --- | --- |
| | after 75 min | after 135 min | after 195 min |
| Sample A | 4.46 | 7.94 | 8.48 |
| Sample B | 0.173 | 0.182 | 0.261 |

The experiment was repeated twice, this result, i.e. the same ratio of the absorption rates, also being found with the corresponding samples 2A and 2B or 3A and 3B.

It was shown as a result of these experiments that on account of ultrasonic treatment in the initial phase, after the application of the buprenorphine-containing patch to the skin
1. the skin penetration rate of this transdermally administered pharmaceutical active compound is increased, and
2. the lag-time was reduced compared with the patch not treated using ultrasound in the initial phase.

What is claimed is:

1. A process for the administration of a transdermally administrable active compound having a low skin penetration rate, comprising the steps:
    a) sticking a skin-adherent patch containing the transdermally administrable active compound onto the skin,
    b) treating the skin-adherent patch solely with ultrasound during an initial phase, and
    c) wearing of the patch during a subsequent long-term phase without additional ultrasonic treatment.
2. The process as claimed in claim 1, where the patch is a transdermal therapeutic system.
3. The process as claimed in claim 1, where the patch contains a layer with a pressure-sensitive adhesive.
4. The process as claimed in claim 1, where the patch contains a porous layer.
5. The process as claimed in claim 1, where the patch contains a layer containing a hydrogel.
6. The process as claimed in claim 1, where the initial phase extends over a period of 1 to approximately 180 minutes.
7. The process as claimed in claim 1, where the initial phase extends over a period of 1 to approximately 60 minutes.
8. The process as claimed in claim 1, where the initial phase extends over a period of 1 to approximately 30 minutes.
9. The process as claimed in claim 1, where the initial phase very particularly preferably extends over a period of 1 to approximately 10 minutes.
10. The process as claimed in claim 1, where the ultrasonic treatment is carried out using a frequency from the range between 20 kHz and 10 MHz.
11. The process as claimed in claim 1, where the ultrasonic treatment is preferably carried out using a frequency from the range between 40 kHz and 1 MHz.
12. The process as claimed in claim 1, where the ultrasonic treatment is carried out using a frequency from the range between 800 kHz and 1 MHz.
13. The process as claimed in claim 1, where the ultrasonic treatment is carried out using an intensity of between 0.01 and 3 W/cm$^2$.
14. The process as claimed in claim 1, where an agent improving the transmission of ultrasonic waves is additionally applied to the patch adhering to the skin.
15. The process as claimed in claim 14, where the agent improving the transmission of ultrasound is an aqueous contact gel.
16. The process as claimed in claim 1 for the treatment of pain.
17. The process as claimed in claim 16, where the pains are chronic and/or acute states of pain.
18. The process as claimed in claim 1, where the transdermally administrable active compound having a low skin penetration rate is an analgesic.
19. The process as claimed in claim 1, where the active compound is selected from the group consisting of morphine, heroin, the derivatives of morphine, the dihydromophine derivatives, hydromorphone, oxycodone, the morphinan derivatives, levorphanol, buprenorphine, the pethidine group, pethidine, ketobemidone, methadone, levomethadone, dextramoramide, fentanyl and its derivatives, the benzomorphan derivatives, pentazocine, the phenylaminocyclohexenyl derivatives and tilidine.
20. A process for the administration of a transdermally administrable active compound having a low skin penetration rate, comprising the steps:
    a) sticking a skin-adherent patch containing the transdermally adrnirustrable active compound onto the skin of a patient,
    b) treating the skin-adherent patch solely with ultrasound during an initial phrase of 1 to approximately 180 minutes, and
    wearing of the patch during a subsequent long-term phase from 1 to 7 days, during which the active compound is transdermally administered through the skin of the patient without additional ultrasonic treatment, wherein the active compound is selected from the group consisting of morphine, heroin, the derivatives of morphine, the diydromophine derivatives, hydromorphone, oxycodone, the morphinan derivatives, levorphanol, buprenorphine, the pethidine group, pethidine, ketobemidone, methadone, levomethadone, dextramoramide, fentanyl and its derivatives, the benzomorphan derivatives, pentazocine, the phenylaminocyclohexenyl derivatives and tilidine.
21. The process according to claim 20, wherein the long-term phase is from 3 to 7 days.

* * * * *